United States Patent
Rabasco et al.

(10) Patent No.: US 6,890,969 B2
(45) Date of Patent: May 10, 2005

(54) POLYMER EMULSION PRESERVATION USING CATIONIC COMPOUNDS

(75) Inventors: John Joseph Rabasco, Allentown, PA (US); Dennis Sagl, Fogelsville, PA (US)

(73) Assignee: Air Products Polymers, L.P., Allentown, PA (US)

( * ) Notice: Subject to any disclaimer, the term of this patent is extended or adjusted under 35 U.S.C. 154(b) by 160 days.

(21) Appl. No.: 09/997,599

(22) Filed: Nov. 29, 2001

(65) Prior Publication Data

US 2002/0099113 A1 Jul. 25, 2002

Related U.S. Application Data

(63) Continuation-in-part of application No. 09/656,318, filed on Sep. 6, 2000, now abandoned.

(51) Int. Cl.$^7$ ................................................ C08K 5/31
(52) U.S. Cl. ................ 523/122; 424/78.31; 424/78.37; 424/405; 524/237
(58) Field of Search ........................... 424/78.31, 78.37, 424/405; 523/122; 524/237

(56) References Cited

U.S. PATENT DOCUMENTS

| | | | | |
|---|---|---|---|---|
| 3,285,959 | A | | 11/1966 | McFarlane ................ 260/567.6 |
| 3,627,871 | A | * | 12/1971 | Groves et al. .............. 514/576 |
| 3,709,804 | A | * | 1/1973 | Lukhovitsky et al. .......... 522/84 |
| 3,915,918 | A | | 10/1975 | Springle, et al. ........... 260/29.6 |
| 3,970,755 | A | | 7/1976 | Gazzard et al. .............. 424/270 |
| 4,655,957 | A | * | 4/1987 | Chromecek et al. ............ 134/7 |
| 4,661,503 | A | | 4/1987 | Martin et al. ................ 514/372 |
| 4,725,623 | A | | 2/1988 | Whitekettle et al. .......... 514/634 |
| 4,902,503 | A | * | 2/1990 | Umemura et al. .............. 514/6 |
| 4,906,385 | A | | 3/1990 | Lyons et al. ................. 210/698 |
| 5,041,463 | A | | 8/1991 | Whitekettle et al. .......... 514/634 |
| 5,049,383 | A | * | 9/1991 | Huth et al. .................. 424/405 |
| 5,125,967 | A | * | 6/1992 | Morpeth et al. ........... 106/18.22 |
| 5,364,874 | A | * | 11/1994 | Morpeth ...................... 514/373 |
| 5,457,083 | A | | 10/1995 | Muia et al. .................. 504/128 |
| 5,583,091 | A | * | 12/1996 | Backhouse et al. ........... 504/149 |
| 5,879,663 | A | * | 3/1999 | Nakabayashi et al. ......... 424/54 |
| 6,017,561 | A | * | 1/2000 | Zhou et al. .................. 424/486 |
| 6,149,927 | A | * | 11/2000 | Ghosh ......................... 424/405 |

FOREIGN PATENT DOCUMENTS

GB          1091049          11/1967          ............ D21H/5/22

OTHER PUBLICATIONS

Hawley's Condensed Chemical Dictionary, 12th Edition, Von Nostrad Reinhol Company, 1993, p. 301.*
El–Zayat and Omran, "Disinfectants Effect on the growth and Metabolism of *Acetobacter aceti*" (*Egypt J–Food–Sci.*, 11(1–2), 1983, pp. 123–128).
*Handbook of Biocide and Preservative Use*, Edited by H. W. Rossmore, Blackie Academic & Professional, 1995, pp. 361–362.
ZENECA Biocides, "*Vantocil® IB Microbiocide*", 1997, ZENECA, Inc.

* cited by examiner

*Primary Examiner*—Peter Szekely
(74) *Attorney, Agent, or Firm*—Mary E. Bongiorno

(57) ABSTRACT

This invention is directed to a method of preserving colloid-stabilized polymer emulsions against microbial attack and spoilage using selected cationic compounds. It is also directed to compositions containing colloid-stabilized polymer emulsions and cationic compounds that are resistant to contamination with biodeteriogenic microbes. It has been discovered that specific cationic compounds are particularly effective against biodeteriogenic microbes in preserving polymer emulsions that have been stabilized with protective colloids, such as poly(vinyl alcohol). Examples of suitable microbicidal cationic compounds are: substituted pyridinium salts, substituted guanidine salts, tetrasubstituted ammonium salts, and polymeric cationic compounds.

22 Claims, No Drawings

POLYMER EMULSION PRESERVATION USING CATIONIC COMPOUNDS

CROSS-REFERENCE TO RELATED APPLICATIONS

This application is a continuation-in-part of application Ser. No. 09/656,318, filed on Sep. 6, 2000, now abandoned.

BACKGROUND OF THE INVENTION

Water based polymer emulsions (latex emulsions) are susceptible to microbial contamination resulting in product spoilage. Polymer emulsions are dispersions of fine organic polymer particles in water. These polymer particles are suspended and stabilized in an aqueous environment with additional organic substrates, such as surfactants and protective colloids. Surfactants, protective colloids, such as poly(vinyl alcohol) and hydroxyethyl cellulose, thickeners and other additives, and the polymer itself all provide a supply of carbon nutrition for microorganisms to metabolize. Polymer emulsions are therefore susceptible to spoilage due to microbial attack and propagation. Standard industrial practices combat such product biodeterioration by the addition of various industrial biocides (antimicrobial agents) directly after the manufacturing process. Examples of commonly used industrial biocides are: 1,2-benzisothiazolin-3-one (BIT), and a blend of 5-chloro-2-methyl4-isothiazolin-3-one (CIT) and 2-methyl-4-isothiazolin-3-one (MIT). Examples of other biocides commonly used for polymer emulsion preservation include 1,2-dibromo-2,4-dicyanobutane (DBDCB), 2,2-dibromo-3-nitrilo-propionamide (DBNPA), 2-bromo-2-nitro-1,3-propanediol (BNPD), aldehyde derivatives, formaldehyde releasing agents, hydantoins, and chlorinated aromatics.

These commonly used biocides are usually adequate to preserve various types of polymer emulsions against most industrial spoilage from bacteria and fungi. However, polymer emulsions stabilized with protective colloids, such as poly(vinyl alcohol) or hydroxyethyl cellulose, and/or non-ionic surfactants, pose additional strains and challenges to many preservative systems. In general, it has been found that this class of polymer emulsion products is more susceptible to spoilage than other polymer emulsions by certain types of microbes. For example, biodeteriogenic microbes that can survive in acidic environments and/or that metabolize alcohols, such as *Gluconoacetobacter liquefaciens* (GABL), have begun to emerge and thrive in polymer emulsions, even in the presence of commonly used industrial biocides. Bio-deteriogenic microbes include bacteria and fungi that can adversely affect the commercial value of products and materials. Some biodeteriogenic microbes have become so well adapted to the environment present in these emulsions, such as poly(vinyl alcohol)-stabilized poly(vinyl acetate-co-ethylene) copolymer emulsions, that the standard industrial biocides are inadequate to prevent product spoilage by this species over the entire product shelf life period; e.g., 6 to 12 months. A significant rise in polymer emulsion biodeterioration problems has resulted in a need to identify more effective preservative systems.

It is known that VOC's (volatile organic compounds), such as unreacted monomers, in polymer emulsions exert some level of a bacteriostatic, if not bacteriocidal, effect, which can inhibit the growth of biodeteriogenic microbes. Recent developments in polymer emulsion technology, in response to regulatory issues and environmental concerns, have lead to reductions in residual VOC and residual monomer levels. Such VOC reductions impact polymer emulsions in many ways. For example: 1) it creates an emulsion environment more conducive to microbial growth, 2) it may permit the emergence of new microorganisms that find the new emulsion environment more hospitable, 3) it poses additional challenges to current preservative technologies, and 4) it creates the need for new preservation methods to prevent biodeterioration over the product's shelf life.

Although there are a significant number of biocides that can kill microorganisms effectively and can provide very good preservation for polymer emulsions and other industrial products, only a limited number of these exhibit acceptably low toxicity to higher organisms, e.g., humans. The choice of effective biocides that can be added to polymer emulsions becomes even more limited when United States Food and Drug Administration (FDA) clearances are required for the polymer emulsion end use. Many polymer emulsions are used to manufacture consumer goods, such as adhesives and papers for food packaging, diapers, paper towels, baby wipes, and feminine hygiene products. As a result of such contact with skin and indirect contact with foods, the polymer emulsions used in these applications must have the appropriate FDA clearances. These FDA clearances are based on favorable toxicological profiles, including no skin sensitization. In order for a polymer emulsion to receive the necessary FDA clearances, all of its constituents, including the preservative technology, must meet FDA's rigorous toxicological criteria when used at concentrations required for satisfactory performance in the polymer emulsion. FDA-approved biocides have use level restrictions. In some cases, the minimum biologically effective concentration is greater than the maximum allowable use level. Typically, this results in premature product bio-contamination and biodeterioration. Additionally, microorganisms continue to evolve and new microorganisms are beginning to appear that exhibit resistance to some of the more common industrial biocidal agents, particularly at the allowable use level. A tightening regulatory environment, specific consumer good manufacturing specifications, public concern, and product liability, further complicates biocide selection and use. For example, isothiazolinones are widely used antimicrobial agents for many consumer products, but their known skin sensitization property causes concern among many consumer goods manufacturers. Such health concerns and microbial resistance are leading to a search for preservation alternatives and new preservation approaches.

Cationic compounds, such as quaternary ammonium compounds, are well known in the antimicrobial art and are widely used as disinfectants for surfaces. For example, they are used to disinfect floors, walls, countertops, equipment surfaces, food contact surfaces, and the like in hospitals, schools, nursing homes, restaurants, and residential homes. Furthermore, combinations of detergents with cationic compounds are widely used formulations for cleaning and dis-infecting or sanitizing such surfaces with a single product. Cationic compounds are also used to inhibit the growth of algae and microorganisms in water, such as in swimming pools. Cationic compounds have been utilized on a limited basis for the preservation of industrial products and to prevent microbial growth in aqueous systems.

GB 1,091,049 (1967) discloses the preparation of bacteriostatic tissue paper by incorporating alkylated guanidine salts during the tissue paper manufacturing process. The guanidine salt is introduced into the paper pulp slurry prior to sheet formation.

U.S. Pat. No. 3,970,755 (Gazzard et al., 1976) discloses biocidal compositions for aqueous systems comprising lauryl benzyl dimethyl ammonium chloride or cetyl trimethyl ammonium chloride, and 1,2-benzoisothiazolin-3-ones.

U.S. Pat. No. 4,661,503 (Martin et al., 1987) discloses a synergistic biocide composition of n-dodecylguanidine hydrochloride (DGH) and a mixture of 5-chloro-2-methyl-4-isothiazolin-3-one and 2-methyl-4-isothiazolin-3-one for treating industrial process waters to prevent the growth of gram negative bacteria and fungi.

U.S. Pat. No. 4,725,623 (Whitekettle et al., 1988) discloses a bactericidal composition for aqueous systems comprising a synergistic aqueous mixture of 2-bromo-2-nitropropane-1,3-diol and n-dodecylguanidine.

U.S. Pat. No. 4,906,385 (Lyons, et al., 1990) discloses the use of water soluble C8–C18 alkyl guanidine salts, especially n-dodecylguanidine hydrochloride, for controlling macroinvertebrate biofouling of industrial cooling water system.

U.S. Pat. No. 5,041,463 (Whitekettle et al., 1991) discloses a bactericidal composition for aqueous systems, such as pulp and paper mill systems, comprising a combination of glutaraldehyde and dodecylguanidine hydrochloride.

U.S. Pat. No. 5,457,083 (Muia et al., 1995) discloses synergistic antimicrobial compositions containing polyether polyamino methylene phosphonates (PAPEMP) and one or more non-oxidizing biocide, such as didecyl dimethyl ammonium chloride, dodecylguanidine hydrochloride, methylene bisthiocyanate, and 5-chloro-2-methyl-4-isothiazolin-3-one. The combination is reported to be useful in aqueous systems in a variety of industrial applications, such as papermaking, paints, adhesives, latex emulsions, and joint cements. Examples show that addition of PAPEMP to a non-oxidizing biocide improves bacterial kills in an aqueous system over 24 hour period.

El-Zayat and Omran, "Disinfectants Effect on the growth and Metabolism of Acetobacter aceti" (*Egypt J-Food-Sci.,* 11(1–2), 1983, pages 123–128) evaluate quaternary ammonium compounds, such as cetyl trimethylammonium bromide, as disinfectants against the growth and metabolism of *Acetobacter aceti*.

*Handbook of Biocide and Preservative Use,* Edited by H. W. Rossmore, Blackie Academic & Professional, 1995, pages 361–362, describes biocidal surfactants for preservation of cosmetics and toiletries. Quaternary amines are reported to be potent antimicrobial substances.

A need remains for a method of protecting polymer emulsions, especially those stabilized with hydroxyl-containing protective colloids and those with low VOC's, against product biodeterioration by microbes. There is also a need for polymer emulsion compositions which are resistant to biodeterioration over their shelf life (about 6 to 12 months).

BRIEF SUMMARY OF THE INVENTION

This invention is directed to a method of preserving colloid-stabilized polymer emulsions against biodeteriogenic microbe attack and spoilage using selected cationic compounds. It is also directed to compositions containing colloid-stabilized polymer emulsions and cationic compounds that are resistant to spoilage by biodeteriogenic microbes. A method for preventing biodeteriogenic microbe contamination in protective colloid-stabilized polymer emulsions involves mising an effective amount of the cationic compound with the polymer emulsion. Examples of specific cationic compounds that are particularly effective in preserving polymer emulsions that have been stabilized with protective colloids, such as poly(vinyl alcohol), against biodeteriogenic microbes are: substituted pyridinium salts, substituted guanidine salts, tetrasubstituted ammonium salts, and polymeric cationic compounds, in which the substitution can be an alkyl, a cycloalkyl, and/or an aryl group of 2 to 18 carbons. The cationic compounds are also particularly effective in preserving polymer emulsions with low VOC's (i.e. less than 1000 ppm VOC).

These cationic compounds are effective as stand-alone preservatives, exhibiting a broad spectrum of microbicidal activity against bacteria and fungi for an extended period of time, or can also be used in combination with other biocides, such as isothiazolinone derivatives.

The cationic compounds are particularly effective in polymer emulsions containing little or no anionic comonomers, anionic surfactants, or other anionic constituents. The preservative efficacy and potency of the cationic compounds can be diminished in the presence of high surface area polymer particles and/or free aqueous phase nonionic surfactant.

The polymer emulsion compositions of this invention can be blended and formulated with other raw materials for use in preparation of adhesives, architectural coatings, paper coatings, nonwoven binders, etc.

DETAILED DESCRIPTION OF THE INVENTION

Polymer emulsions of this invention are dispersions of synthetic polymers and copolymers in aqueous media. The basic raw materials used to manufacture the polymer emulsions are monomers, initiators, and stabilizers. Examples of monomers include vinyl acetate, ethylene and other olefins, diolefins such as butadiene, various alkyl acrylates, various alkyl methacrylates, styrene, vinyl chloride, vinyl esters, acrylamides, methacrylamides, N-methylolacrylamides, maleates, and others known in the art. Examples of polymer emulsions for purposes of this invention include emulsions of poly(vinyl acetate), poly(vinyl acetate) copolymers such as poly(vinyl acetate-co-ethylene) (VAE), poly(vinyl acetate-acrylics) such as poly(vinyl acetate-butyl acrylate) and poly(vinyl acetate-(2-ethyl)hexyl acrylate), polyacrylics, polymethacrylics, poly(styrene-acrylics), wherein acrylics can include $C_3$–$C_{10}$ alkenoic acids, such as acrylic acid, methacrylic acid, crotonic acid and isocrotonic acid and their esters, other polystyrene copolymers, poly (vinyl chloride-co-ethylene) copolymers, and the like. These polymer emulsions can be stabilized with various surfactants known in the art or with protective colloids, such as hydroxyethyl cellulose or poly(vinyl alcohol), and others known in the art. Polymer emulsions particularly suitable for this invention are stabilized with hydroxyl-containing protective colloids, especially poly(vinyl alcohol). When anionic or nonionic surfactants are used, polymer emulsions must be augmented with a sufficient concentration of cationic compound to compensate for the antagonistic effect of the surfactants. Polymer emulsions with less than 1000 ppm VOC's are also particularly suitable for this invention. Among the VOC's present in polymer emulsions are unreacted monomers, acetic acid, methanol, acetaldehyde, and formaldehyde.

Poly(vinyl alcohol) used in this invention, generally, has a weight average molecular weight ($M_w$) ranging from about 5,000 to 300,000, preferably 10,000 to 200,000. Alternatively, the poly(vinyl alcohol) can have a degree of polymerization of from 100 to 5,000, preferably 200 to 3500. Poly(vinyl alcohol) is made commercially by the hydrolysis of poly(vinyl acetate) and typically has a hydrolysis level ranging from about 85% to greater than 99%. For this invention, the level of hydrolysis can range from 70% to greater than 99%, preferably 85% to 98%. Mixed poly(vinyl alcohol) grades, using combinations of poly(vinyl alcohol)s varying in molecular weight and hydrolysis level, can also be employed. The molecular weight and hydrolysis level are such that the poly(vinyl alcohol) is at least partially soluble in an aqueous medium.

Microbial contamination of polymer emulsions can lead to a range of effects, including color changes, odors, viscosity changes, pH changes, and visible surface growth. It is known in the art that polymer emulsions are susceptible to contamination by a broad range of biodeteriogenic microbes. Examples of microorganisms found to contaminate polymer emulsions include, *Aeromonas hydrophilia, Alcaligenes faecalis, Corynebacterium ammoniagenes, Enterobacter aerogenes, Escherichia coli, Klebsiella pneumoniae, Pseudomonas aeruginosa, Proteus vulgaris, Providencia rettgeri, Pseudomonas stutzeri, Shewanella putrefaciens, Serratia liquefaciens, Acinetobacter baumannii, Burkholderia cepacia, Chryseobacterium meningosepticum, Sphingobacterium spiritivorum, Ralstonia pickettii,* GABL, *Geotrichum candidum, Aspergillus* species, *Sporothrix* species, *Trichoderma viride, Cladosporium* species, *Rhodoturula glutinis, Candida guillermondi, Penicillium* species, and *Candida tropicalis*.

Acceptable cationic compounds for the preservation of the polymer emulsions of this invention include, substituted guanidine salts such as DGH, substituted pyridinium salts such as cetylpyridinium chloride (CPC), tetrasubstituted ammonium salts such as didecyldimethylammonium chloride and alkyldimethyl benzalkonium chloride, biguanides, polymeric cationic derivatives, and the like, in which the substitution is an alkyl, a cycloalkyl, or an aryl group of 2 to 18 carbons. Preferred cationic derivatives include, alkylguanidine salts and alkylpyridinium salts in which the alkyl group contains 2 to 18 carbons. Alkylguanidine salts, especially DGH, are most preferred.

The cationic compounds can be added to the polymer emulsion at any point during the polymer emulsion manufacturing process; preferably, the cationic compound is added to the polymer emulsion as the last additive in the post-manufacturing process. The total amount or dosage of the cationic compound that is added to a polymer emulsion for preservation against microbial contamination can range from 10 ppm to 1 wt %, preferably 50 ppm to 5000 ppm, based on the wet weight of the polymer emulsion.

The use of an alkylguanidine salt, specifically DGH, was unexpectedly found to be very potent and effective for killing and inhibiting the growth of biodeteriogenic microbes, such as GABL, that may contaminate poly(vinyl alcohol) stabilized polymer emulsions, especially vinyl acetate-based polymer emulsions. However, it has been unexpectedly discovered that slight changes in the vinyl acetate-based polymer emulsion composition, such as incorporation of anionic constituents, can have a dramatic influence on the preservative efficacy and potency of alkylguanidine salts. Not intending to be bound by theory, differences in DGH preservative efficacy can be attributed to an unfavorable or competitive interaction of the cationic DGH with the anionic surfactants and/or anionic components present in some of these emulsions. Such interaction can serve to deplete the concentration of the cationic compound in the aqueous phase where it is needed to exert its microbicidal activity.

The preservative efficacy of DGH can also be affected adversely by the presence of nonionic surfactants. For example, the preservative efficacy of DGH can be diminished in vinyl acetate-based polymer emulsions stabilized with a combination of protective colloids and nonionic surfactants.

The cationic compounds are particularly effective in polymer emulsions containing little or no anionic substituents, and little or no anionic or nonionic surfactants. By little is meant nonionic surfactants below their critical micelle concentration and anionic surfactants or substituents below the molar concentration of the added cationic compound.

The cationic compounds of this invention can be used alone or together with other known industrial biocides; for example, BIT, CIT, MIT, DBDCB, DBNPA, DNPD, aldehyde derivatives, such as glutaraldehyde and formaldehyde, formaldehyde releasing agents, such as dimethyloldimethyl hydantoin, imidazolidinyl urea derivatives, polymethoxy bicyclic oxazolidine, and 1-(3-chloroallyl)-3,5,7-triaza-1-azoniaadamantane hydrochloride, hydantoins, phenols, such as sodium o-phenyl phenylate, and chlorinated aromatics, such as chlorhexidene, p-chloro-m-cresol, and chloroxylenol.

In addition, the polymer emulsion compositions of this invention can be blended or formulated with other raw materials for use in preparation of adhesives, architectural coatings, paper coatings, nonwoven binders, etc., provided that those raw materials do not impart sufficient anionic character to inactivate the cationic biocides. For example, although the polymer emulsion compositions of this invention may be used neat for adhesive applications, such polymer emulsion compositions are often formulated depending upon the specific end use.

When formulated for adhesive compositions, the polymer emulsion compositions of this invention are typically present in the adhesive composition at levels ranging from 60 to 90 parts by weight. Common additives used in the formulation of adhesive compositions include, plasticizers, defoamers, thickeners, dispersants, crosslinkers, humectants, tackifiers, poly(vinyl alcohol), and fillers.

Representative plasticizers include glycols, such as dipropylene glycol, dibenzoate types, such as dipropylene glycol dibenzoate and diethylene glycol dibenzoate, phthalates, such as dibutyl phthalate, and liquid polyesters, such as triethylene glycol polyester of benzoic acid and phthalic acid, and others known in the water-based adhesion art. The plasticizer is typically used at levels ranging from 2 to 30 parts by weight.

Representative defoamers include silicon or hydrocarbon based materials. The defoamer is typically used at levels of 0 to 1 part by weight.

Representative thickeners include, casein, fumed silica, guar gum, bentonite, alginates, starches, hydroxyethyl cellulose, other cellulosics, polyether polyols, and other thickeners known in the water-based adhesion art. Thickeners are typically used at levels of 0 to 5 parts by weight.

Representative crosslinkers include dialdehydes, such as glutaraldehyde, metals, such as zinc and zirconium, melamine formaldehyde resins, diepoxides and epoxy resins. Crosslinkers are typically used at levels of 0 to 10 parts by weight.

Representative humectants include, calcium chloride, glycols, glycerine, ureas, sorbitol, and others known in the water-based adhesion art. Humectants are typically incorporated at levels of 0 to 20 parts by weight.

Representative tackifiers include, gum rosin, ester gum, hydrocarbon resins, hydrogenated rosin, tall oil rosins, terpene resins, and others known in the water-based adhesion art. Tackifiers are typically used in their dispersion form and used at levels of 0 to 35 parts by weight in adhesive compositions.

Poly(vinyl alcohol) in the formulation can have a weight average molecular weight ($M_w$) ranging from about 5,000 to 300,000, preferably 10,000 to 200,000. Alternatively, the poly(vinyl alcohol) can have a degree of polymerization of from 100 to 5,000, preferably 200 to 3500. It is typically used at levels of 0 to 10 parts by weight.

Representative fillers include, calcium carbonate, clay, mica, silica, talc, and others known in the water-based adhesion art. Fillers are typically used at levels 0 to 40 parts by weight.

Depending upon the level of formulation, it may be required to add additional amounts of the cationic biocide to compensate for the dilution from the formulation additives in order to produce a water-based adhesive composition that is resistant to biodeteriogenic microbe contamination.

The invention will be further clarified by a consideration of the following examples, which are intended to be purely exemplary of the invention.

The preservative efficacy of several cationic compounds was examined by adding various dosage levels of the compounds to several poly(vinyl alcohol)-stabilized poly (vinyl acetate-ethylene) (VAE) copolymer emulsions, some of which contain less than 1000 ppm vinyl acetate monomer. The resulting polymer emulsions were then subjected to stringent biochallenge testing, the details of which are described below.

EXAMPLE 1

The preservative efficacy of several cationic compounds in a poly(vinyl alcohol)-stabilized VAE copolymer emulsion ($T_g$=0) containing less than 1000 ppm vinyl acetate monomer was assessed according to the following procedure:

Test Microorganism: GABL

GABL Inoculum Preparation

A recently isolated culture of GABL was grown on potato dextrose agar slants by inoculating the agar surface. The potato dextrose agar slants were incubated for 48–72 hours at 25° C. After this incubation period, GABL cells were harvested using quarter strength Ringers solution to wash the GABL colonies off of the agar surface. The washings from each slant were combined into one sterile, Erlenmeyer flask. The number of slants and the amount of quarter strength Ringers solution used to wash off the GABL colonies was adjusted during the procedure to obtain a final microbial viable count in the range of $10^8$–$10^{10}$ CFU/mL.

Rapid Automated Bacterial Impedance Technique (RABIT): supplied by Microbiology International, manufactured by Don Whitley Scientific, Ltd.

RABIT utilizes the principal of impedance microbiology to detect and assess microbial activity in a given sample. Using the RABIT, microbial metabolism is monitored by measuring the amount of carbon dioxide produced by actively respiring microorganisms. The electrodes in the RABIT test cells are partially covered with alkaline agar containing potassium hydroxide. As inoculated test samples are monitored on the RABIT, carbon dioxide produced from microbial metabolism is absorbed by the alkaline agar resulting in a change in conductivity. Conductivity is monitored with time and the time to reach a pre-specified rate of reduction in conductivity is termed the time to detection (TTD). Therefore, the shorter the TTD, the higher the number of microorganisms present. Failure can be defined as three successive decreases in conductivity equal to or greater than a pre-specified value (−10 microSiemens is recommended by the manufacturer) at any time during the 72 hour RABIT monitoring period. Alternatively, failure can be defined as a pre-specified total change in conductivity.

Biochallenge Test Procedure

Samples (50 g each) of each test emulsion containing a test antimicrobial agent were inoculated with 1.0 mL of the GABL inoculum. After mixing well, the samples were then placed in a 30° C. incubator. After 1, 2, and 6 days of incubation each sample was streak plated onto potato dextrose agar to assess the level of surviving GABL microorganisms. The potato dextrose agar plates were incubated at 25° C. for 48–72 hours before assessing the growth. On the seventh day of incubation, each test emulsion sample was inoculated again with a freshly prepared GABL inoculum, mixed well, then placed back into the incubator. The samples were again streak plated onto potato dextrose agar after incubating for 1, 2, and 6 days since the second inoculation. On the fourteenth day after the test was initiated, the test emulsions were inoculated a third time with another freshly prepared GABL inoculum and then placed back into the incubator. The samples were again streak plated onto potato dextrose agar after 1, 2, 6, and 13 days of incubation since the third inoculation to assess surviving microorganisms. Test failure is defined as a microbial viable count >300 CFU/10 $\mu$L observed from the potato dextrose agar streak plate assessments.

Biochallenge Test Procedure Via the RABIT

A small amount of a microbial nutrient was added to each emulsion test sample (50 g) containing a test antimicrobial agent. The resulting samples were then inoculated with 1.0 mL of the GABL inoculum. After mixing well, an aliquot (5 g) of each test sample was placed into separate RABIT indirect conductivity tubes. The indirect conductivity tubes were then placed into the RABIT incubator modules set at 30° C. and the conductivity changes monitored for up to 72 hours. The remainder of each test sample was stored in a 30° C. incubator during the RABIT monitoring period. At the completion of the RABIT monitoring period, the aliquot samples were placed back into their respective sample containers. Each test sample was then re-inoculated with a freshly prepared GABL inoculum. After mixing well, an aliquot (5 g) of each test sample was again placed into fresh RABIT indirect conductivity tubes and monitored on the RABIT as before. This inoculation and RABIT conductivity monitoring procedure was repeated every three to four days until sample failure or until several inoculations were passed without failure.

Results

Table 1 shows the efficacy of various types of cationic compounds compared to standard industrial biocides to control and inhibit the growth of GABL in a VAE copolymer emulsion having a $T_g$ of 0° C. and stabilized solely with a partially hydrolyzed poly(vinyl alcohol) and containing less than 1000 ppm vinyl acetate monomer. It is clear from the data that there were dramatic differences in preservative efficacy in this polymer emulsion environment depending upon the type of cationic compound or biocide used. For example, a dosage of 200 ppm DGH exhibited outstanding microbicidal activity against GABL by controlling and inhibiting GABL growth through 7 inoculations of the GABL inoculum. Similar dosages of poly (hexamethylenebiguanide) hydrochloride, chlorhexidine, cetyltrimethylammonium bromide (CTAB), and benzalkonium derivatives were ineffective, failing the test immediately after the initial GABL inoculation. Higher dosage levels of these cationic compounds are necessary to attain suitable preservative efficacy. The common industrial biocides, such as CIT/MIT, DBNPA, DBDCB, and glutaraldehyde were all inferior preservatives. The use of CIT/MIT was limited to 50 ppm and DBNPA was limited to 100 ppm, due to sensitization issues and FDA regulations. An additive effect was achieved with a combination of CIT/MIT and DGH. CPC, an active antimicrobial agent found in over the counter mouthwashes, was also effective against the GABL, passing 5 inoculations at a 300 ppm dosage. Didecyldimethylammonium chloride or other dialkyldimethyl ammonium chlorides at 200 ppm were moderately effective under these testing conditions by inhibiting GABL growth through 2 to 3 inoculations. These results were unexpected since other known anti-microbial materials, such as glutaraldehyde, DBDCB, and DBNPA, were ineffective against GABL, even at doses of 450 and 500 ppm.

TABLE 1

| Biocide | Biocide Type | Biocide Dosage* | Inoculations Passed[a] |
|---|---|---|---|
| Blank (no biocide) | — | 0 | 0 |
| 3:1 CIT/MIT | Isothiazolinone | 15 ppm | 0 |
| 3:1 CIT/MIT | Isothiazolinone | 45 ppm | 2 |
| DGH | Cationic | 50 ppm | 1 |
| DGH | Cationic | 100 ppm | 2 |
| DGH | Cationic | 200 ppm | 7 |
| 3:1 CIT/MIT + DGH | Isothiazolinone + cationic | 40 ppm + 100 ppm | 4 |
| Glutaraldehyde | Aldehyde | 500 ppm | 0 |
| DBDCB | Organobromine | 450 ppm | 0 |
| DBNPA | Organobromine | 100 ppm | 0 |
| Troysan ® 395 4:1 Mixture of 1,3-Bis(hydroxymethyl)-5,5-dimethylhydantoin and Hydroxymethyl-5,5-dimethylhydantoin | Formaldehyde Releaser | 1000 ppm | 0 |
| CPC | Cationic | 100 ppm | 0 |
| CPC | Cationic | 250 ppm | 2 |
| CPC | Cationic | 300 ppm | 5 |
| CTAB | Cationic | 300 ppm | 1 |
| Chlorhexidine digluconate | Cationic | 250 ppm | 0 |
| Chlorhexidine diacetate | Cationic | 400 ppm | 0 |
| Vantocil ® IB Poly(hexamethylenebiguanide) hydrochloride | Cationic | 250 ppm | 0 |
| Vantocil IB | Cationic | 400 ppm | 2 |
| Poly(dimethylaminodiallylamine) chloride | Cationic | 500 ppm | 0 |
| TPI ® 1716 Didecyldimethylammonium chloride | Cationic | 100 ppm | 0 |
| TPI 1716 | Cationic | 200 ppm | 2 |
| TPI 1716 | Cationic | 300 ppm | ≧5 |
| TPI ® 1717 Benzalkonium chloride | Cationic | 200 ppm | 0 |
| TPI 1717 | Cationic | 300 ppm | 0 |
| BTC ® 2125M $C_{12}$–$C_{18}$ - Alkyldimethyl benzalkonium chlorides and $C_{12}$–$C_{14}$-alkyldimethyl ethylbenzalkonium chlorides | Cationic | 200 ppm | 0 |
| BTC 2125M | Cationic | 300 ppm | ≧5 |
| BT ® 824 $C_{12}$–$C_{18}$ - Alkyldimethyl benzalkonium chlorides | Cationic | 200 ppm | 0 |
| BTC 824 | Cationic | 300 ppm | ≧5 |
| BTC ® 818 $C_8$ and $C_{10}$ - dialkyldimethyl ammonium chloride | Cationic | 200 ppm | 2 |
| BTC 818 | Cationic | 300 ppm | ≧5 |
| BTC ® 1010 Didecyldimethylammonium chloride | Cationic | 100 ppm | 0 |
| BTC 1010 | Cationic | 200 ppm | 3 |
| BTC 1010 | Cationic | 300 ppm | ≧5 |
| BTC ® 776 $C_{12}$–$C_{18}$ - Alkyldimethyl benzalkonium chlorides and alkyldimethyl methylbenzalkonium chlorides | Cationic | 200 ppm | 0 |
| BTC ® 776 | Cationic | 300 ppm | ≧5 |
| Busan ® WSCP Poly[oxyethylene(dimethyliminio)ethylene (dimethyliminio) ethylene dichloride] | Cationic | 500 | 0 |
| Citricidal ® ammoniated grapefruit seed extract. | Cationic | 2000 ppm** | 0 |
| Glycine | Amino Acid | 500 ppm | 0 |
| Tolcide ® PS | Cationic | 500 ppm | 0 |
| Tetrakis(hydroxymethyl) phosphonium sulfate | Phosphorus | | |
| Valine | Amino Acid | 1000 ppm | 0 |

*Active ingredient
**As supplied by manufacturer; the active amount was not known because the manufacturer did not provide the product composition
BTC 818, 824, 1010, and 2125M supplied by Stepan Company
Busan WSCP supplied by Buckman Laboratories
TPI 1716 and 1717 supplied by Schulke & Mayr (Germany)
Tolcide PS supplied by Albright & Wilson
Vantocil IB supplied by Avecia Biocides
Troysan 395 supplied by Troy Corporation

EXAMPLE 2

The procedure described in Example 1 was followed, except that the preservative efficacy of DGH was further examined by varying its dosage concentration and varying the polymer emulsion composition. Data from the procedure are compiled in Table 2.

The ability of DGH to protect and preserve polymer emulsions against the growth of GABL was dramatically different depending upon the polymer emulsion type and composition. For example, DGH was extremely robust and effective in controlling GABL growth in poly(vinyl alcohol)-stabilized VAE copolymer emulsions. However, at the same dosage levels, DGH exhibited no preservative efficacy in VAE copolymer emulsions that contain substantial amounts of anionic comonomer or anionic surfactant. Furthermore, the preservative efficacy of DGH was lessened when certain initiation systems, such as persulfate/sodium formaldehyde sulfoxylate, were used to manufacture the VAE emulsion. The preservative efficacy of DGH was also reduced by the presence of substantial amounts of nonionic surfactant.

TABLE 2

| Emulsion Polymer | | | | # of GABL Inoculations Passed DGH Dosage | | |
|---|---|---|---|---|---|---|
| Co-monomers | ~$T_g$, °C. | Initiator | Stabilization | 100 ppm | 150 ppm | 200 ppm |
| VA/E | 14 | $H_2O_2$/SFS | PVOH | 5 | ≧7[a] | ≧7[a] |
| VA/E | 20 | $H_2O_2$/SFS | PVOH | ≧4[b] | ≧4[b] | ≧4[b] |
| VA/E | 0 | $H_2O_2$/SFS | PVOH | 3 | 4 | ≧7[a] |
| VA/E | 0 | $H_2O_2$/SFS | PVOH | 2 | ND | 7 |
| VA/E | −15 | $H_2O_2$/SFS | PVOH | 2 | 5 | ≧7[a] |
| VA/E | 4 | KPS/SFS | Nonionic surfactant/HEC | 0 | 0 | 0 |
| VA/E/AA | 0 | $H_2O_2$/SFS | PVOH/nonionic surfactant | ND | ND | 0 |

TABLE 2-continued

| Emulsion Polymer | | | | # of GABL Inoculations Passed DGH Dosage | | |
|---|---|---|---|---|---|---|
| Co-monomers | ~$T_g$, °C. | Initiator | Stabilization | 100 ppm | 150 ppm | 200 ppm |
| VA/E | −5 | $H_2O_2$/SFS | PVOH/ nonionic surfactant | 1 | 3 | 3 |
| VA/E/MA/ SVS | 5 | KPS/SFS | Nonionic surfactant | 0 | 0 | 0 |
| VA/E | 0 | $H_2O_2$/SFS | PVOH/ nonionic surfactant | 1 | 2 | 2 |
| VA/E | 8 | KPS/SFS | PVOH | ND | ND | 2 |
| VA/E/SVS/ NMA | 10 | TBHP/sodium erythorbate | Anionic sulfate surfactant | ND | ND | 0 |

[a]GABL biochallenge stopped after 7th inoculation.
[b]GABL biochallenge stopped after 4th inoculation.
VA = vinyl acetate. E = ethylene. AA = acrylic acid comonomer. MA = maleic anhydride comonomer. SVS = sodium vinyl sulfonate comonomer. NMA = N-methylolacrylamide comonomer.
KPS = potassium persulfate. TBHP = tert-butylhydrogen peroxide. SFS = sodium formaldehyde sulfoxylate.
HEC = hydroxyethyl cellulose. PVOH = poly(vinyl alcohol).
ND = no data.

EXAMPLE 3

The preservative efficacy of several cationic compounds in a poly(vinyl alcohol)-stabilized VAE copolymer emulsion ($T_g$=0) containing less than 1000 ppm vinyl acetate was assessed according to the following procedure:
Test Microorganisms

*Aeromonas hydrophilia, Alcaligenes faecalis, Corynebacterium ammoniagenes, Enterobacter aerogenes, Escherichia coli, Klebsiella pneumoniae, Pseudomonas aeruginosa, Proteus vulgaris, Providencia rettgeri, Pseudomonas stutzeri, Shewanella putrefaciens, Serratia liquefaciens, Acinetobacter baumannii, Burkholderia cepacia, Chryseobacterium meningosepticum, Sphingobacterium spiritivorum, Ralstonia pickettii,* and GABL.
Mixed Bacterial Pool Inoculum Preparation Each bacterial culture was individually grown on nutrient agar slants, except GABL was grown on potato dextrose agar slants, by inoculating the agar surfaces. The nutrient agar slants were incubated for 24–48 hours at 30° C. and the potato dextrose agar slants were incubated for 48–72 hours at 25° C. After this incubation period, the cells were harvested using quarter strength Ringers solution to wash the bacterial colonies off the agar surface. The washings from all of the slants were combined into one sterile, Erlenmeyer flask. The number of slants and the amount of Ringers Solution used to wash off the bacterial colonies is adjusted during the procedure to obtain a final mixed microbial viable count in the range of $10^8$–$10^{10}$ CFU/mL.
Bacterial Biochallenge Test Procedure The RABIT procedures were followed as described in Example 1, except the mixed bacterial pool inoculum was used to inoculate the test samples instead of the GABL inoculum.

The broad spectrum preservative efficacy of DGH and CPC against various bacterial species is demonstrated in Table 3. DGH again showed the most potency and efficacy compared to the other cationic compounds. At 200 ppm dosage, DGH inhibited the growth of a mixed bacterial pool through 7 inoculations. At 400 ppm, CPC was as effective as DGH at 200 ppm.

TABLE 3

| Biocide | Active Biocide Dosage | Inoculations Passed |
|---|---|---|
| Blank (no biocide) | 0 | 0 |
| CIT/MIT | 40 ppm | 3 |
| DGH | 100 ppm | 2 |
| DGH | 200 ppm | 7 |
| Poly(hexamethylenebiguanide) hydrochloride | 250 ppm | 0 |
| Poly(hexamethylenebiguanide) hydrochloride | 400 ppm | 4 |
| CPC | 300 ppm | 5 |
| CPC | 400 ppm | 7 |
| Poly(dimethylaminodiallylamine) chloride | 500 ppm | 0 |

EXAMPLE 4

The antifungal preservative efficacy of various cationic compounds in a poly(vinyl alcohol)-stabilized VAE copolymer emulsion ($T_g$=0) containing less than 1000 ppm vinyl acetate was assessed according to the following procedure:
Yeasts: *Rhodoturula glutinis, Candida guillermondi,* and *Candida tropicalis.*
Molds: *Geotrichum candidum, Aspergillus* species, *Sporothrix* species, *Trichoderma viride,* and *Cladosporium* species.
Mixed Yeast Inoculum Preparation Each yeast culture was individually grown on potato dextrose agar plates by inoculating the agar surface. The potato dextrose agar plates were then incubated for 3–7 days at 25° C. After this incubation period, the yeast cells were harvested using quarter strength Ringers solution to wash the colonies off the agar surface. The washings were combined into a sterile, Erlenmeyer flask. The number of plates used and the amount of Ringers solution used to wash off the cells is adjusted during the procedure to ultimately obtain a final microbial count in the range of $10^6$–$10^7$ CFU/mL.
Mixed Mold Inoculum Preparation Each mold culture was individually grown on potato dextrose agar plates by inoculating the agar surface. The potato dextrose agar plates were then incubated for 3–7 days at 25° C. After this incubation period, the mold cells were harvested using a 0.005% dioctyl sulfosuccinate aqueous solution to wash the colonies off the agar surface. The washings were filtered through sterile cheesecloth and the filtrates combined into one sterile, Erlenmeyer flask. The number of plates used and the amount of 0.005% dioctyl sulfosuccinate used to wash off the cells is adjusted during the procedure to obtain a final microbial count in the range of $10^6$–$10^7$ CFU/mL.
Fungal Biochallenge Test Procedure Each test sample (50 g) of polymer emulsion containing a test antimicrobial agent was inoculated with 0.5 mL of the mixed yeast inoculum. After mixing well, the opened sample containers were then placed into a larger second container containing 20 g of sterile vermiculite and 80 g of sterile water. Each test sample was then inoculated with 0.5 mL of the mixed mold inoculum by gently distributing the mold inoculum over the entire surface of the emulsion test sample. The samples were not mixed further. With minimal disturbance of the test sample surfaces, covers were placed onto the larger vermiculite containers leaving the smaller emulsion test sample container open inside the vermiculite container. The samples were then incubated for 28 days at 25° C. After the 28 day incubation period, the vermiculite containers were opened without disturbing the test sample surfaces and the presence of any surface fungal growth was visually assessed. After recording these observations as no growth, slight growth, moderate growth, heavy growth, or dense growth, the samples were thoroughly mixed and each was streak plated onto potato dextrose agar to assess the level of surviving microorganisms. The potato dextrose agar plates were incubated at 25° C. for 3–5 days before growth assessment.

Table 4 displays the preservative efficacy data of specific cationic compounds against yeasts and molds. The poly (vinyl alcohol) stabilized poly(vinyl acetate-co-ethylene) copolymer emulsion containing 200 ppm DGH provided good protection against molds or yeasts. The most efficacious preservatives against yeast and molds was either 300 ppm CPC or a combination of 40 ppm CIT/MIT and 200 ppm DGH.

TABLE 4

| Biocide | Surface Fungal Growth | Growth on PDA |
| --- | --- | --- |
| Blank (no biocide) | Dense Growth | Dense |
| 75 ppm DGH | Dense Growth | Dense |
| 100 ppm DGH | Dense Growth | Dense |
| 200 ppm DGH | Moderate Growth | Very Slight |
| 40 ppm CIT/MIT/ 100 ppm DGH | Moderate Growth | Very Slight |
| 40 ppm CIT/MIT/ 200 ppm DGH | No Growth | No Growth |
| 300 ppm CPC | No Growth | No Growth |

What is claimed is:

1. An aqueous polymer emulsion composition resistant to biodeteriogenic microbe contamination comprising a poly (vinyl alcohol) stabilized aqueous polymer emulsion combined with a cationic compound selected from the group consisting of a substituted guanidine salt, a polymeric cationic compound, and mixtures thereof, wherein the substituted guanidine salt is substituted with an alkyl, a cycloalkyl, or an aryl group containing 2 to 18 carbons, said cationic compound in an amount effective for preventing biodeteriogenic microbe contamination of said polymer emulsion, said polymer emulsion containing little or no nonionic or anionic surfactants and little or no anionic substituents.

2. The polymer emulsion composition of claim 1, wherein the cationic compound is selected from the group consisting of n-dodecylguanidine hydrochloride, poly (hexamethylenebiguanide) hydrochloride, and mixtures thereof.

3. The polymer emulsion composition of claim 1, wherein the cationic compound is n-dodecylguanidine hydrochloride.

4. The polymer emulsion composition of claim 1 further comprising one or more other industrial biocide.

5. The polymer emulsion composition of claim 4 wherein the one or more other industrial biocide is 5-chloro-2-methyl-4-isothiazolin-3-one, 2-methyl-4-isothiazolin-3-one, or mixtures thereof.

6. The polymer emulsion composition of claim 1 wherein the polymer emulsion is selected from the group consisting of a poly(vinyl acetate-co-ethylene), poly(vinyl acetate), poly(vinyl acetate-butyl acrylate), poly(vinyl acetate-(2-ethyl)hexyl acrylate), and poly(vinyl chloride-co-ethylene).

7. The polymer emulsion composition of claim 6 wherein the polymer emulsion is a poly(vinyl acetate-co-ethylene) or a poly(vinyl acetate).

8. A method for preventing biodeteriogenic microbe contamination in a poly(vinyl alcohol) stabilized polymer emulsion comprising:

mixing an effective amount for preventing biodeteriogenic microbe contamination of a cationic compound with said polymer emulsion, said cationic compound selected from the group consisting of a substituted guanidine salt, a polymeric cationic compound, and mixtures thereof, wherein the substituted guanidine salt is substituted with an alkyl, a cycloalkyl, or an aryl group containing 2 to 18 carbons said polymer emulsion containing little or no nonionic or anionic surfactants and little or no anionic substituents.

9. The method of claim 8, wherein the cationic compound is selected from the group consisting of n-dodecylguanidine hydrochloride, poly(hexamethylenebiguanide) hydrochloride, and mixtures thereof.

10. The method of claim 8, wherein the cationic compound is n-dodecylguanidine hydrochloride.

11. The method of claim 8 further comprising mixing one or more other industrial biocide with the polymer emulsion.

12. The method of claim 11 wherein the one or more other industrial biocide is 5-chloro-2-methyl-4-isothiazolin-3-one, 2-methyl-4-isothiazolin-3-one, or mixtures thereof.

13. The method of claim 8 wherein the polymer emulsion is selected from the group consisting of a poly(vinyl acetate-co-ethylene), poly(vinyl acetate), poly(vinyl acetate-butyl acrylate), poly(vinyl acetate-(2-ethyl)hexyl acrylate), and poly(vinyl chloride-co-ethylene).

14. The method of claim 13 wherein the polymer emulsion is a poly(vinyl acetate-co-ethylene) or a poly(vinyl acetate).

15. The method of claim 8, wherein the amount of the cationic compound ranges from 10 ppm to 1 wt %, based on the wet weight of the polymer emulsion.

16. The method of claim 8, wherein the amount of the cationic compound ranges from 50 ppm to 5000 ppm, based on the wet weight of the polymer emulsion.

17. An adhesive composition comprising the aqueous polymer emulsion composition of claim 1, wherein said adhesive composition is resistant to biodeteriogenic microbe contamination.

18. The adhesive composition of claim 17 which comprises:

30 to 90 parts by weight of the aqueous polymer emulsion composition of claim 1;

2 to 30 parts by weight of a plasticizer;

0 to 5 parts by weight of a thickener;

0 to 20 parts by weight of a humectant;

0 to 35 parts by weight of a tackifier;

0 to 10 parts by weight of poly(vinyl alcohol); and 0 to 40 parts by weight of a filler.

19. An aqueous polymer emulsion composition resistant to biodeteriogenic microbe contamination comprising a poly (vinyl alcohol) stabilized aqueous polymer emulsion combined with 10 to 400 ppm, based on the wet weight of said polymer emulsion, of a cationic compound selected from the group consisting of a substituted guanidine salt, a substituted pyridinium salt, a tetrasubstituted ammonium salt, a polymeric cationic compound, and mixtures thereof, wherein the substituted guanidine salt and the substituted pyridinium salt are substituted with an alkyl, a cycloalkyl, or an aryl group containing 2 to 18 carbons and the tetrasubstituted ammonium salt is substituted with one or more of an alkyl, a cycloalkyl, and/or an aryl, said polymer emulsion containing little or no nonionic or anionic surfactants and little or no anionic substituents, said cationic compound effective in said amounts for preserving protective colloid stabilized polymer emulsions.

20. The polymer emulsion composition of claim 19, wherein the cationic compound is selected from the group consisting of n-dodecylguanidine hydrochloride, cetyl pyridinium chloride, didecyldimethylammonium chloride, poly (hexamethylenebiguanide) hydrochloride, and mixtures thereof.

21. A method for preventing biodeteriogenic microbe contamination in a poly(vinyl alcohol) stabilized polymer emulsion comprising:

mixing said polymer emulsion with 10 to 400 ppm, based on the wet weight of polymer emulsion, of a cationic compound selected from the group consisting of a substituted guanidine salt, a substituted pyridinium salt, a tetrasubstituted ammonium salt, a polymeric cationic compound, and mixtures thereof, wherein the substituted guanidine salt and the substituted pyridinium salt are each individually substituted with an alkyl, a cycloalkyl, or an aryl group containing 2 to 18 carbons and the tetrasubstituted ammonium salt is substituted with one or more of an alkyl, a cycloalkyl, and/or an aryl, said polymer emulsion containing little or no nonionic or anionic surfactants and little or no anionic substituents.

22. The method of claim 21, wherein the cationic compound is selected from the group consisting of n-dodecylguanidine hydrochloride, cetyl pyridinium chloride, didecyldimethylammonium chloride, poly (hexamethylenebiguanide) hydrochloride, and mixtures thereof.

* * * * *